(12) United States Patent
Shaw

(10) Patent No.: US 11,617,894 B2
(45) Date of Patent: Apr. 4, 2023

(54) POWER LIMITER IN AN ELECTROCONVULSIVE THERAPY DEVICE

(71) Applicant: Mecta Corporation, Tualatin, OR (US)

(72) Inventor: John B. Shaw, Aloha, OR (US)

(73) Assignee: BALANCE POINT, LLC, Tualatin, OR (US)

( * ) Notice: Subject to any disclaimer, the term of this patent is extended or adjusted under 35 U.S.C. 154(b) by 0 days.

(21) Appl. No.: 17/209,019

(22) Filed: Mar. 22, 2021

(65) Prior Publication Data

US 2021/0290966 A1 Sep. 23, 2021

Related U.S. Application Data

(60) Provisional application No. 62/992,805, filed on Mar. 20, 2020.

(51) Int. Cl.
*A61N 1/04* (2006.01)
*A61N 1/38* (2006.01)

(52) U.S. Cl.
CPC ............ *A61N 1/38* (2013.01); *A61N 1/046* (2013.01)

(58) Field of Classification Search
CPC .................................. A61N 1/38; A61N 1/046
See application file for complete search history.

(56) References Cited

U.S. PATENT DOCUMENTS

| | | | |
|---|---|---|---|
| 5,755,744 A * | 5/1998 | Shaw ..................... | A61N 1/38 607/45 |
| 2005/0165458 A1* | 7/2005 | Boveja ............... | A61N 1/37217 607/45 |
| 2008/0161883 A1* | 7/2008 | Conor .................... | A61N 1/321 607/48 |

* cited by examiner

*Primary Examiner* — Ankit D Tejani
*Assistant Examiner* — Joshua Brendon Solomon
(74) *Attorney, Agent, or Firm* — Miller Nash LLP

(57) ABSTRACT

An ElectroConvulsive Therapy (ECT) device for generating a series of electrical therapeutic pulses for delivery to a patient to cause a seizure includes a user interface configured to accept one or more therapy settings from a user, a therapy generator configured to generate the series of electrical therapeutic pulses, and a therapy delivery system structured to apply the series of electrical therapeutic pulses to the patient. The ECT device further includes a power monitor configured to measure average electrical power that is being delivered to the patient through the series of electrical therapeutic pulses in real-time during a treatment session, and to cause the therapy generator to cease operation after a predetermined threshold level of average electrical power has been delivered to the patient. Related methods are also disclosed.

18 Claims, 3 Drawing Sheets

POWER LIMITER IN AN ELECTROCONVULSIVE THERAPY DEVICE

CROSS-REFERENCE TO RELATED APPLICATIONS

This application is a non-provisional of and claims benefit from U.S. provisional patent application No. 62/992,805, titled FAILSAFE POWER LIMITER IN AN ELECTROCONVULSIVE THERAPY DEVICE, filed Mar. 20, 2020, the disclosure of which is incorporated herein by reference in its entirety.

FIELD OF THE INVENTION

This disclosure is directed to systems and methods related to delivering electroconvulsive therapy, and, more particularly, to a power limiter in an electroconvulsive therapy delivery device.

BACKGROUND

An ElectroConvulsive Therapy (ECT) device delivers, under control of a physician, pulses of therapeutic electrical current to treat a variety of psychiatric illnesses and their associated symptoms. The delivered pulses are intended to induce a seizure in the patient, which, in some cases, helps alleviate or substantially address the patient's underlying illness or symptoms. Before treatment, the patient is anesthetized to minimize the severity of the muscle convulsion effects of the treatment.

In an ECT device, the therapeutic pulses are delivered to a patient through a pair of treatment electrodes. The electrodes are connected to the patient at a specially prepared skin site, and a conductive gel is applied between the electrode and the patient's skin to reduce electrical impedance. The static impedance of the skin-to-electrode contact is verified through the ECT device prior to any treatment to ensure safety of the patient during treatment.

As is well known from accidents involving exposed wiring and lightning strikes, too much electricity flowing into a patient's skin can cause physical burns. It is important, therefore, to prevent electrical energy from flowing from an ECT device into a patient at a rate that is too high for the body to naturally absorb the heat created by the infusion of electrical energy into the skin.

Embodiments of the invention address these and other limitations of the state of the art.

DESCRIPTION

Figure 1:
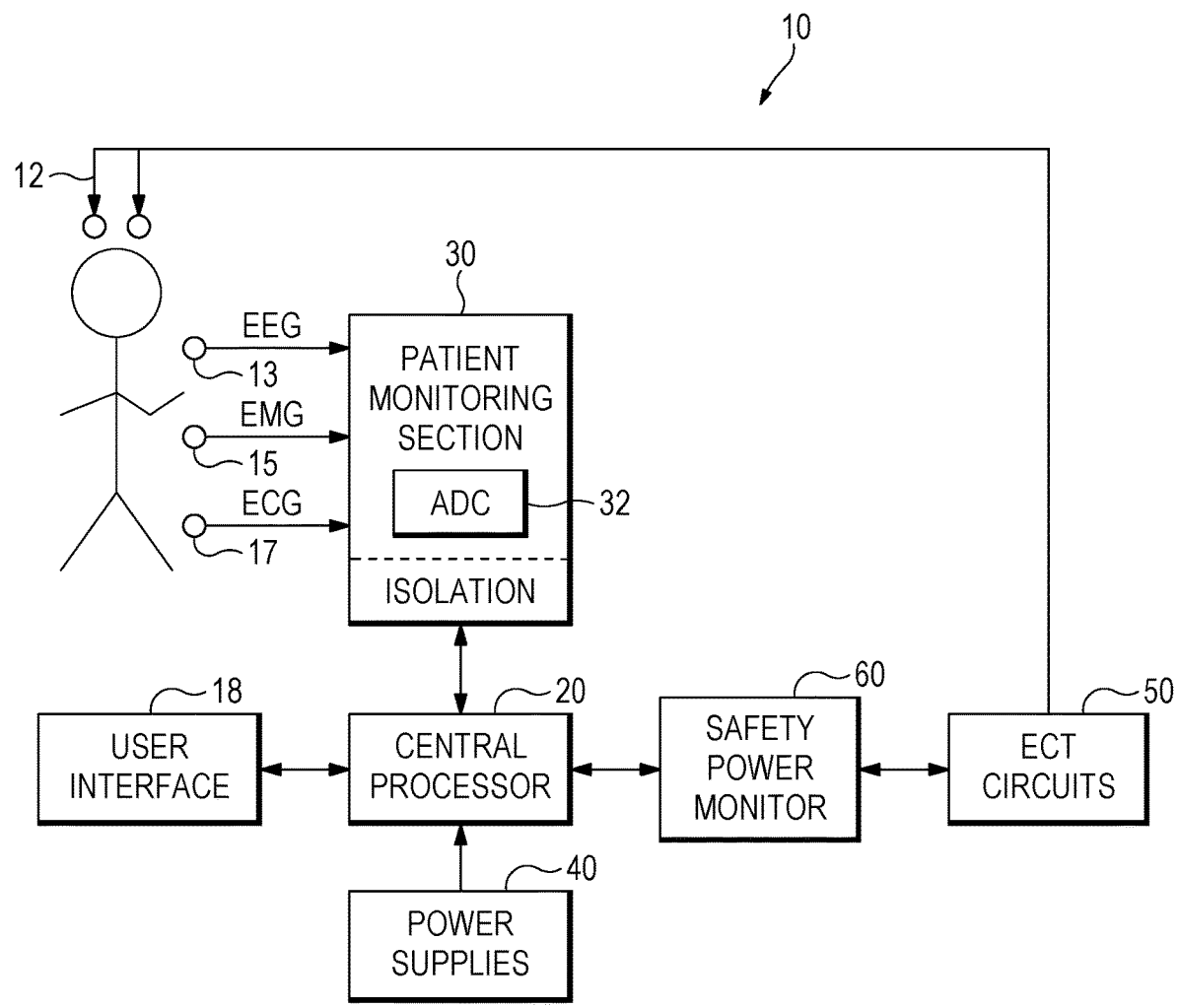
FIG. 1 is a functional block diagram of an ElectroConvulsive Therapy (ECT) system with safety power monitoring according to embodiments of the disclosed technology.

FIG. 1 is a functional block diagram of an ElectroConvulsive Therapy (ECT) system 10 with safety power monitoring in accordance with various embodiments of the disclosed technology. A particular embodiment of an example ECT system 10 is described in greater detail in U.S. Pat. Nos. 5,755,744 and 6,014,587, which are herein incorporated by reference in their entirety.

Referring to FIG. 1, an ECT system 10 includes two main types of connections with the patient. The first type of connection between the patient and the ECT system 10 is for patient monitoring. Patient monitoring may include one or more sets of electrodes that are used to sense electrical signals from the patient. Such monitoring includes, for example, receiving electroencephalography (EEG) signals, electromyography (EMG) signals, and/or electrocardiography (ECG) signals from the patient, which may be received through electrodes 13, 15, and 17, respectively. The second type of connection between the patient and the ECT system 10 is for delivering therapeutic pulses to the patient. These pulses are generated by the system 10, under control of a physician, and delivered to the patient through a set of therapy electrodes 12.

The overall system 10 further includes a user interface 18 through which the user, typically a psychiatrist or other medical doctor, interacts or interfaces with the ECT system 10. The user interface 18 may include a touch screen, for example. In other embodiments the user interface 18 may be a series of input switches and knobs.

The user interface may further include a display screen by which the system 10 may display information to the user both prior to and during treatment. Such information may include traces of patient waveforms collected by the monitoring inputs 13, 15, 17. It may also include information about the amount or level of therapeutic energy or electrical power to be delivered to the patient, or the amount or level of therapeutic energy or electrical power that has already been delivered to the patient in the present session. The user interface 18 may also include a chart recorder to provide a hard copy output of the patient monitoring signals and/or records of the therapeutic pulses delivered to the patient.

A central processor 20 orchestrates the operation of the ECT system 10. The central processor 20 may perform or control a number of various functions of the ECT system 10, such as controlling the user interface 18, performing safety checks on various internal devices and parameters, receiving patient information, generating the therapeutic ECT signal, creating a record of the treatment sessions, and generally performing the main operations of the ECT system 10, among other functions.

The central processor 20 is also coupled to a patient monitoring section 30 to configure the patient monitoring section 30 into various modes, as well as to receive monitoring data from the patient. The patient monitoring section 30 includes an Analog to Digital Converter (ADC) 32 to digitize the incoming patient monitoring signals. In preferred embodiments, the patient monitoring section 30 is isolated from other portions of the ECT system 10 to prevent electrical shock hazards due to contact with other electrical equipment as required by international IEC 60601 standards.

One or more power supplies 40 provide electrical power to operate the system 10 as well as the power used to generate the ECT therapy signal. The ECT therapy signal is generated and managed, in the illustrated embodiment, by an ECT circuit block 50. In most cases, delivering ECT pulses through treatment electrodes to the scalp of an anesthetized psychiatric patient is intended to trigger a seizure, which seizures are generally therapeutic in treating certain psychiatric disorders and their symptoms. The level of electrical power delivered to the patient by the ECT system 10 is monitored and limited by a safety power monitor 60, which is coupled to the ECT circuit block 50 and to the central processor 20.

Embodiments of the disclosed technology use the safety power monitor 60 to ensure that the electrical energy delivered from the ECT system 10 to the patient through the stimulus electrodes 12 is always delivered at a low enough rate to prevent any patient burns at the interface of the skin and stimulus electrodes. As described above, electrical energy absorbed through a patient's skin may cause a burn if the electrical energy is delivered at a rate too high for the body to absorb the heat that such power delivery causes.

Electric charge is measured in coulombs (C), with one coulomb defined as a specific number of elementary charges. Coulombs flowing through an electrical conductor over time is defined as electric current (I), and is measured in amperes. One ampere is the flow of electric charge at the rate of one coulomb per second. Electric current passing through an electric potential difference, also known as a voltage difference or merely as voltage (V), is electric power. Electric power is measured in Watts (W). The formula for electric power is $P=VI$, so that the electric power in Watts is equal to a circuit's voltage (V) times its electric current (I), in Amps. Wattage can also be expressed as $P=VQ/t$, which is a circuit's voltage (V) multiplied by the number of coulombs (C) flowing through a conductor over time (t).

The wattage of electrical power entering the body is one factor when determining a safe threshold of delivering electrical pulses as therapy. Another factor is the area of the skin to which the electrical power is being delivered. As the area of skin receiving electrical power from the ECT system 10 is directly related to the area of the therapy delivery electrodes 12, the size of the delivery electrodes may be used in calculating the maximum level of electrical power that the body may safely receive without burning. In one embodiment the therapy delivery electrodes 12 are round electrodes having a diameter of approximately 2 inches. With electrodes of this size, a safe level of electrical power that can be delivered to a patient through a pair of such electrodes without burning the skin is approximately 100 Watts for typical stimulus delivery times of 8 seconds or less. Although it is possible that some patients may be able to withstand more than 100 Watts delivered into 2 inch therapy electrodes 12 and not be burned, the 100 Watt number was chosen to ensure no patients would incur skin burns at that level of delivery. If the therapy electrodes 12 were larger, that is, had a greater surface area, then the 100 Watt safety threshold could be increased with the same amount of safety. In some embodiments the electric power safety threshold may be modified by a user. In the preferred embodiment, however, the electric power safety threshold of the ECT system 10 is set by the manufacturer, and cannot be adjusted.

Another factor in setting the safety threshold at 100 Watts is that the therapy electrodes 12 are properly attached to the patient in the proper manner. The ECT system 10 performs a static impedance check of the circuit from the system 10, through the first therapy delivery electrode 12, through the patient's skin, through the second therapy delivery electrode 12, and back to the system 10. A static impedance that is above a safe level may be caused by an insufficient amount of contact gel being used between the patient and the therapy delivery electrode, or by an electrode that is not completely attached to the patient. A static impedance that is below the safe level may be caused by the electrodes 12 being attached too close to one another or by contact gel that is not contained directly under the therapy electrodes. The ECT system 10 may not generate a therapeutic pulse if the static impedance of the therapy electrodes is outside safety parameters.

Figure 2:
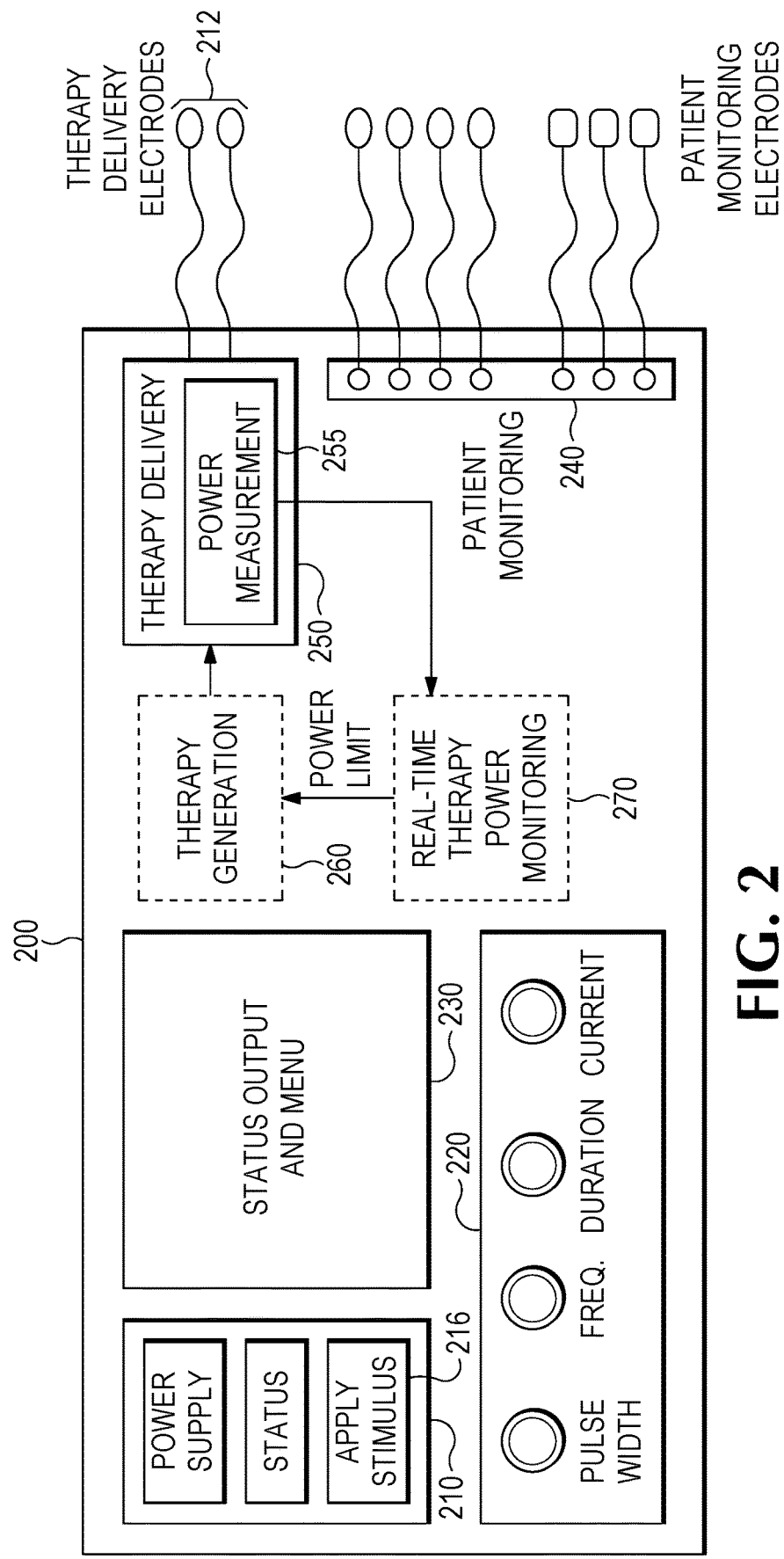
FIG. 2 is a functional block diagram of an ECT device, which may be an example of the ECT system of FIG. 1 according to embodiments of the disclosed technology.

FIG. 2 is a functional block diagram of an ECT device 200, which may be an example of the ECT system 10 of FIG. 1.

The ECT Device 200 generally includes a user control and information block 210 where the user can perform various functions, such as turning on the device 200, monitoring its status, as well as includes a button or control 216 to apply a stimulus to a patient. The apply stimulus control 212 may be located on a remote control in addition to or instead of a panel mounted control. A stimulus control interface 220 allows the user to shape the therapeutic waveform and define the parameters that will be applied to the patient as the ECT therapy stimulus. Such parameters may include, for example, the frequency of the signal, the pulse width of each individual pulse in the signal, the electric current level, and the duration of the ECT signal.

One set of a certain number of ECT therapy pulses continually applied to the patient having the specified parameters is referred to as a stimulus delivery. Typically, only one stimulus delivery of approximately ½-8 seconds is made to the patient in each therapy session, although the stimulus delivery duration could be shorter or longer. It is possible, however, for the doctor to apply more than one stimulus delivery during a treatment session. Typically, stimulus deliveries would be separated by several tens of seconds or even minutes, during which time the patient would be observed.

A screen 230, which may be a touchscreen, accepts user input and generates output for the user, such as various reports about the delivered therapy, as described below.

A patient monitoring block 240 accepts leads from various patient monitoring systems, as described above. The monitoring systems may include, for example, EEG, ECG and EMG signals received from the patient. The monitoring systems may also include an Optical Monitoring System (OMS), which generates patient monitoring data through optical monitoring methods.

A therapy delivery block 250 is responsible for delivering the stimulus to the patient, through one or more stimulus electrodes 212 connected to the delivery block, when the user causes the ECT device 200 to apply its stimulus to the patient. A power measurement block 255 measures the instantaneous electrical power delivered to the patient, in real-time. In one embodiment the power measurement block 255 includes a transformer placed in the circuit that delivers the therapeutic pulses through the stimulus electrodes 212. The transformer generates an instantaneous current signal that, when combined with an instantaneous voltage measurement, accurately measures the instantaneous power being applied to the patient, in real-time as the therapy signal is being applied to the patient. In one embodiment an instantaneous voltage corresponding to the instantaneous power may be measured directly from a circuit within the therapy delivery block 250 that drives the delivery electrodes 212 themselves. This operation of measuring the instantaneous power being applied to the patient in real-time and how it is used to limit a maximum electric power level applied to the patient is described in further detail below.

A therapy generation block 260 is an electrical signal generation block that generates the ECT stimulus therapy for delivery to the patient through the therapy delivery block 250. The therapy generation block 260 is illustrated in dashed lines as it is an internal component to the ECT device 200 and normally not visible to the user.

A real-time therapy power monitoring block 270 functions to actively monitor the therapy stimulus that is delivered by the therapy delivery block 250 to the patient, in real-time. When the level of power delivered to the patient exceeds the pre-determined limits, such as 100 Watts, the power monitoring block 270 sends a signal to the therapy generation block 260 to immediately shut down, and stop producing therapy signals. In some embodiments, after receiving the power limit signal from the power monitoring block 270, the therapy generation block 260 goes into a complete reset mode, and will not generate further therapy until the ECT device 200 is completely restarted. In some embodiments the power monitoring block 270 could send its power limit exceeded signal directly to the therapy delivery block 250, which would then cause the therapy delivery block 250 to prevent delivery of the ECT therapy to the patient.

By discontinuing ECT therapy when the predefined power threshold has been exceeded, embodiments of the invention prevent burns from occurring on a patient skin by limiting the level of electric power applied to the patient during therapy.

The real-time therapy power monitoring block 270 may operate independently from and in addition to any voltage and/or electrical current monitoring systems described in the incorporated descriptions. No other monitoring and/or warning systems in the ECT device 200 or ECT device 10 measures the level of electric power being delivered to the patient, in real-time, and compares that level of electric power to a pre-determined threshold.

Figure 3:
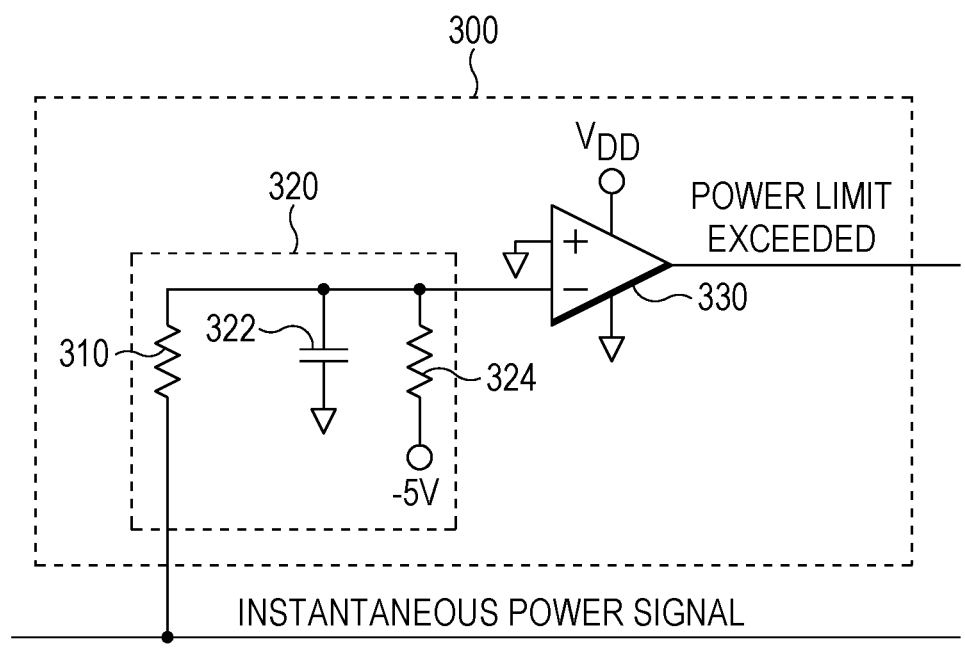
FIG. 3 is a schematic diagram illustrating an example embodiment of a safety power monitor for use in safety power monitoring according to embodiments of the disclosed technology.

FIG. 3 illustrates an example embodiment of a power monitor 300, which may be an embodiment of the real-time therapy power monitoring block 270 of FIG. 2. The power monitor 300 includes a resistor 310 coupled to the therapy delivery signal that is being monitored. More specifically, the resistor 310 is coupled to an instantaneous power signal that is generated by monitoring the therapy delivery block 250 of FIG. 2. In some embodiments the instantaneous power signal is a voltage signal produced by multiplying the instantaneous current by the instantaneous voltage of the therapy delivery system of an ECT device. The instantaneous power signal is a real-time indication of the amount of power delivered to the patient.

The instantaneous power signal is fed to a pass-through filter 320, which is formed by a resistor 310, capacitor 322 and another resistor 324. The filter 320 has a time constant tuned for the particular desired power threshold. In some embodiments the resistor 324 has one end coupled to a negative voltage, such as −5V. An operational amplifier 330 accepts the electrical signal coupled to the common node of the resistor 310, the capacitor 322 and resistor 324 at its inverting input, while its non-inverting input is coupled to ground or to another reference voltage. The output of the operational amplifier 330 is a power limit exceeded signal. This power limit exceeded signal, when activated, indicates that the level of electric power applied to the patient through the ECT device 10 exceeds the pre-determined threshold. The output of the operational amplifier 330 is normally HIGH, until the threshold has been exceeded, in which case the output of the operational amplifier 330 immediately goes LOW. When the therapy generation block 260 of FIG. 2 receives a LOW power limit exceeded signal, the therapy generation block 260 immediately stops generating new therapy pulses. In some embodiments receiving a LOW power limit exceeded signal causes the therapy generation block 260 to go into a reset mode. Of course, whether the power monitor 300 generates a LOW signal output or a HIGH signal output to signify an error condition is an implementation decision. In either case, the therapy generation block 260 would act as described above after receiving the error signal from the power monitor 300 to stop generating new therapy pulses and/or enter a reset mode.

In operation, when the power monitor 300 starts up, the power limit exceeded signal output from the operational amplifier 330 is HIGH, because the inverting input of the operational amplifier 330 is coupled to a negative voltage. The negative voltage is produced by the voltage divider consisting of resistor 310 connected to the instantaneous power signal which is initially 0 volts, and resistor 324 connected to −5 volts. The capacitor 322 is charged to this negative voltage.

When the ECT device 200 begins delivering therapeutic ECT pulses through the therapy electrodes 212 to the patient, the power measurement block 255 (FIG. 2) measures the electrical power delivered to the patient, in real time. In the embodiment illustrated in FIG. 3, this measurement is in the form of voltage pulses of the instantaneous power signal coupled to the resistor 310, with a voltage pulse generated each time a therapeutic ECT pulse is applied to the patient. The voltage pulses are positive pulses, and range from 0 V to 3 V, for example.

Each voltage pulse sensed at the resistor 310 charges the capacitor 322 a small amount from its initial reference voltage. Between pulses, the capacitor 322 partially discharges. Each subsequent pulse further charges the capacitor 322. This circuit produces a voltage directly corresponding to the average power delivered to the patient. If the voltage pulses on the instantaneous power signal were to stop before the output of the operational amplifier 322 changed from HIGH to LOW, then the capacitor 322 would gradually lose charge back toward its reference voltage at a rate determined by the time constant of the pass-through filter 320. Such a process is what happens when an entire therapy stimulus is delivered to the patient without exceeding the pre-determined power level. Also, such a process is the typical process, in which the entire therapy stimulus is delivered to the patient at an electric energy delivery rate low enough to prevent skin burns. In other words, it would be the exception for the power monitor 300 to ever output its power limit exceeded signal.

If instead the voltage pulses on the instantaneous power signal continue to charge the capacitor 322 until it is above zero volts, then the output of the operational amplifier 300 immediately switches from HIGH to LOW, and the predefined power limit has been exceeded. In this case, the power limit exceeded signal of the power monitor 300 switches to LOW.

Setting the pre-determined power limit is a function of setting the charging and discharging time constants of the pass-through filter 320 in relation to the level and time spacing of the voltage pulses generated on the instantaneous power signal line that is coupled to the pass-through filter 320. The time constants of the pass-through filter 320 may be changed by modifying the resistance value of resistor 310, the capacitance value of the capacitor 322, the resistance value of the resistor 324, and/or by modifying the reference voltage also coupled to the resistor 324. In some embodiments the resistor 310 may have a value of approximately 63.4 KΩ, the resistor 324 may have a value of approximately 499 KΩ, and the capacitor 322 may have a value of 0.47 μF. Of course, other values may be possible for these components to create the desired time constant. Further, although embodiments of the invention are tuned to create a time constant that generates the safety signal at approximately 100 Watts, other power thresholds are possible by adjusting the time constant of the power monitor 300 in the manner described above.

The power measurement block 255 of FIG. 2 preferably measures the therapy delivery signal for as long as the ECT therapy delivery is applied to the patient. As mentioned above, an ECT therapy stimulus delivery typically lasts for less than eight seconds, and more typically between ½ and 8 seconds. In some embodiments the time constant of the pass-through filter 322 is set to trigger the output of the operational amplifier 300 after approximately ½ second of receiving voltage pulses from the instantaneous power signal.

As the charge on capacitor 322 increases with each delivered pulse, the charge drained off between pulses also increases. As the delivery continues, either the power limit threshold is exceeded and the power limit exceeded signal is sent, or the charge added to capacitor 322 and the charge drained off during each pulse cycle balance out, in which case the monitor stabilizes and never sends the power limit exceeded signal.

Although the power monitor 300 is described with reference to FIG. 3 as an analog electrical device, it is possible in other embodiments of the invention to implement the power monitor 300 using digital methods. In such an embodiment the delivered voltage and current for each pulse might be measured and multiplied together to obtain instantaneous power. This could be multiplied by the pulse width to determine the energy in the pulse. This could then be divided by the time between the beginning of successive pulses to compute the average power. Each such average could be compared to a number indicative of a pre-determined power threshold. If an average exceeded the pre-determined power threshold, then an output of the digital version of the power monitor 300 could generate the appropriate power limit exceeded signal to cause the therapy generation block 260 (FIG. 2) to shut down, and to discontinue generating any therapy signal. Of course other embodiments are possible using other implementations of the described invention.

Aspects of the disclosure may operate on particularly created hardware, firmware, digital signal processors, or on a specially programmed computer including a processor operating according to programmed instructions. The terms controller or processor as used herein are intended to include microprocessors, microcomputers, Application Specific Integrated Circuits (ASICs), and dedicated hardware controllers. One or more aspects of the disclosure may be embodied in computer-usable data and computer-executable instructions, such as in one or more program modules, executed by one or more computers (including monitoring modules), or other devices. Generally, program modules include routines, programs, objects, components, data structures, etc. that perform particular tasks or implement particular abstract data types when executed by a processor in a computer or other device. The computer executable instructions may be stored on a computer readable storage medium such as a hard disk, optical disk, removable storage media, solid state memory, Random Access Memory (RAM), etc. As will be appreciated by one of skill in the art, the functionality of the program modules may be combined or distributed as desired in various aspects. In addition, the functionality may be embodied in whole or in part in firmware or hardware equivalents such as integrated circuits, FPGA, and the like. Particular data structures may be used to more effectively implement one or more aspects of the disclosure, and such data structures are contemplated within the scope of computer executable instructions and computer-usable data described herein.

All features disclosed in the specification, including the claims, abstract, and drawings, and all steps or operations in any method or process disclosed, may be combined in any combination, except combinations where at least some of such features and/or steps are mutually exclusive. Each feature disclosed in the specification, including the claims, abstract, and drawings, can be replaced by alternative features serving the same, equivalent, or similar purpose, unless expressly stated otherwise.

The disclosed aspects may be implemented, in some cases, in hardware, firmware, software, or any combination thereof. The disclosed aspects may also be implemented as instructions carried by or stored on one or more or computer-readable storage media, which may be read and executed by one or more processors. Such instructions may be referred to as a computer program product. Computer-readable media, as discussed herein, means any media that can be accessed by a computing device. By way of example, and not limitation, computer-readable media may comprise computer storage media and communication media.

I claim:

1. An ElectroConvulsive Therapy (ECT) device structured to generate a series of electrical therapeutic pulses for delivery to a patient to cause a seizure, the device comprising:
   a user interface configured to accept one or more therapy settings from a user;
   a therapy generator configured to generate the series of electrical therapeutic pulses;
   a therapy delivery system structured to apply the series of electrical therapeutic pulses to the patient; and
   a power monitor configured to:
   measure average electrical power that is being delivered to the patient through the series of electrical therapeutic pulses in real-time during a treatment session by a filter having a time constant related to a pre-determined threshold level of average electrical power delivered to the patient, and
   cause the therapy generator to cease operation after more than the predetermined threshold level of average electrical power has been delivered to the patient.

2. The ECT device according to claim 1, in which the power monitor is structured to generate a power limit exceeded signal when the patient has received more than the predetermined threshold amount of average electrical power during the treatment session.

3. The ECT device according to claim 2, in which the therapy generator is structured to prevent generation of the series of electrical therapeutic pulses after the power limit exceeded signal is received from the power monitor.

4. The ECT device according to claim 2, in which the therapy delivery system is structured to prevent the delivery of the series of electrical therapeutic pulses to the patient after the power limit exceeded signal is received from the power monitor.

5. A method for providing protection in an ElectroConvulsive Therapy (ECT) device structured to generate a series of electrical therapeutic pulses for delivery to a patient to cause a seizure, the method comprising:
   measuring the average amount of electrical power that is being delivered to the patient through the series of electrical therapeutic pulses during a stimulus delivery period by a filter having a time constant related to a predetermined threshold level of electrical power; and preventing application of further delivery of electrical therapeutic pulses to the patient after the patient has received more than the pre-determined threshold level of average electrical power in the stimulus delivery period.

6. The method of claim 5, in which monitoring an average amount of electrical power that is being delivered to the patient comprises monitoring an instantaneous voltage of a capacitor in the filter.

7. The ECT device according to claim 1, in which the predetermined threshold level of average electrical power is set by a manufacturer of the ECT device, and cannot be adjusted by a user.

8. The ECT device according to claim 1, in which the filter is a pass-through filter.

9. The ECT device according to claim 8, in which the time constant is a discharging time constant, and in which the discharging time constant is determined at least in part by selecting a capacitance value of a capacitor in the filter, and by selecting a resistance value of a resistor in the filter.

10. The ECT device according to claim 9, in which the filter further includes a charging time constant determined at least in part by selecting a resistance value of a second resistor in the filter, the second resistor coupled to an instantaneous power signal that represents the series of electrical therapeutic pulses in real-time during the treatment session.

11. The ECT device according to claim 8, in which an output of the pass-through filter is coupled to an input of a threshold comparator.

12. The ECT device according to claim 11, in which the threshold comparator is an operation amplifier having an inverting input coupled to the output of the pass-through filter, and having a non-inverting input coupled to a reference voltage.

13. The method of claim 5, in which the predetermined threshold level of average electrical power is set by a manufacturer of the ECT device, and cannot be adjusted by a user.

14. The method of claim 5, in which the filter is a pass-through filter.

15. The method of claim 5, in which the time constant is a discharging time constant, and in which the discharging time constant is determined at least in part by selecting a capacitance value of a capacitor in the filter, and by selecting a resistance value of a resistor in the filter.

16. The method of claim 15, in which the filter further includes a charging time constant determined at least in part by selecting a resistance value of a second resistor in the filter, the second resistor coupled to a signal representing the series of electrical therapeutic pulses delivered to the patient.

17. The method of claim 8, further comprising passing an output of the pass-through filter to an input of a threshold comparator.

18. The method of claim 17, in which the threshold comparator is an operation amplifier having an inverting input coupled to the output of the pass-through filter, and having a non-inverting input coupled to a reference voltage.

* * * * *